(12) United States Patent
Sarfaty et al.

(10) Patent No.: US 7,046,019 B1
(45) Date of Patent: May 16, 2006

(54) DIRECT NON CONTACT MEASUREMENT

(75) Inventors: Moshe Sarfaty, Cupertino, CA (US); Sven Hermann, Sunnyvale, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 0 days.

(21) Appl. No.: 11/034,122

(22) Filed: Jan. 12, 2005

(51) Int. Cl.
G01R 31/26 (2006.01)
H01L 21/66 (2006.01)

(52) U.S. Cl. ............... 324/751; 324/765; 438/14
(58) Field of Classification Search ....... 324/750–754, 324/97, 716, 765; 356/630, 369, 504; 250/307, 250/310; 438/14, 17
See application file for complete search history.

(56) References Cited

U.S. PATENT DOCUMENTS 6,787,773 B1 * 9/2004 Lee .............................. 250/311
2004/0130718 A1 * 7/2004 Krishnan .................... 356/369

* cited by examiner

Primary Examiner—Vinh Nguyen
Assistant Examiner—Arleen M. Vazquez
(74) Attorney, Agent, or Firm—Luedeka, Neely & Graham, P.C.

(57) ABSTRACT

A method of measuring a lower similar layer that is separated from an upper similar layer by an intervening dissimilar layer in an integrated circuit. A first electron beam having a first relatively lower landing energy is directed at the integrated circuit. The first relatively lower landing energy is sufficient to completely penetrate the upper similar layer and insufficient to completely penetrate the intervening dissimilar layer, thereby producing first readings that are characteristic of the upper similar layer. A second electron beam having a second relatively higher landing energy is directed at the integrated circuit, the second relatively higher landing energy is sufficient to completely penetrate the upper similar layer, the intervening dissimilar layer, and the lower similar layer, thereby producing second readings that are characteristic of both the upper similar layer and the lower similar layer. The first readings that are characteristic of the upper similar layer are subtracted from the second readings that are characteristic of both the upper similar layer and the lower similar layer, to produce third readings that are characteristic of only the lower similar layer.

20 Claims, 1 Drawing Sheet

DIRECT NON CONTACT MEASUREMENT

FIELD

This invention relates to the field of integrated circuit fabrication. More particularly, this invention relates to measurement tools that are used during the integrated circuit fabrication process.

BACKGROUND

Integrated circuits are fabricated by forming a layer, performing some type of processing in regard to that formed layer—such as etching—and then forming an overlying layer. This process is repeated many times until the completed integrated circuit is formed.

As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

It is often very desirable to know certain properties of a given layer within an integrated circuit. However, some layers do not adopt their final properties until other layers are formed on top of them, or they are otherwise unavailable for convenient measurement until they are buried underneath the subsequently formed layers.

One example of such a layer is the gate insulation layer. The gate insulation layer is traditionally formed of a very thin silicon oxide layer, or more recently of a very thin high k layer, such as oxides of heavy and rare earth metals having higher dielectric constants and higher capacitances, such as $HfSiON$, $ZrO_2$, $ZrSiON$, $HfO_2$, $HfON$, $La_2O_3$, $CeO_2$, $Na_2O_3$, $Sm_2O_3$, $Eu_2O_3$, $Gd_2O_3$, $Tb_2O_3$, $Dy_2O_3$, $HO_2O_3$, $Er_2O_3$, $Tm_2O_3$, $Yb_2O_3$, and $Lu_2O_3$.

The existing methods to measure gate insulation layers are predominantly optical techniques, ellipsometry, XPS, and X-ray-electron spectroscopy. These techniques suffer from various drawbacks. For example, some require a relatively large measurement spot size, and are therefore used on monitor substrates only because they are not appropriate for production substrates, which have very small features. Further, some of these techniques are used on exposed gate insulation layers. When the gate insulation layer is capped with the gate electrode layer, these measurement techniques are not able to measure the underlying gate insulation layer.

Another possible method is to use an electron probe micro analysis technique, which can penetrate down through the gate electrode layer to the gate insulation layer. However, in this case the measurement of the gate insulation layer is confounded by a native oxide layer that forms on the top surface of the gate electrode layer, and which in many instances will have a comparable thickness.

Unfortunately, the native oxide thickness is generally unknown, and tends to be relatively non-uniform both across the substrate and from substrate to substrate. Not knowing the thickness of the native oxide introduces a large variation and inaccuracy into the measurement of an extremely thin gate insulation layer.

What is needed, therefore, is a system that overcomes problems such as those described above, at least in part.

SUMMARY

The above and other needs are met by a method of measuring a lower similar layer that is separated from an upper similar layer by an intervening dissimilar layer in an integrated circuit. A first electron beam having a first relatively lower landing energy is directed at the integrated circuit. The first relatively lower landing energy is sufficient to completely penetrate the upper similar layer and insufficient to completely penetrate the intervening dissimilar layer, thereby producing first readings that are characteristic of the upper similar layer.

A second electron beam having a second relatively higher landing energy is directed at the integrated circuit, the second relatively higher landing energy is sufficient to completely penetrate the upper similar layer, the intervening dissimilar layer, and the lower similar layer, thereby producing second readings that are characteristic of both the upper similar layer and the lower similar layer. The first readings that are characteristic of the upper similar layer are subtracted from the second readings that are characteristic of both the upper similar layer and the lower similar layer, to produce third readings that are characteristic of only the lower similar layer.

In this manner, measurements can be taken on the lower layer after overlying layers have been formed, and the properties of any similar overlying layers can be removed from the measurements. In addition, the method enables measurement at a very small spot, rather than from a large structure. Thus, readings can be taken on patterned production substrates, rather than just on monitor substrates.

In various embodiments according to this aspect of the invention, the first electron beam and the second electron beam are produced at two different times by one electron beam generator. Alternately, the first electron beam and the second electron beam are produced by pulsing one electron beam generator back and forth between the first relatively lower landing energy and the second relatively higher landing energy. In other embodiments the first electron beam and the second electron beam are produced by two separate electron beam generators. Further yet, the first electron beam and the second electron beam may be produced simultaneously by two separate electron beam generators.

The relatively lower landing energy is preferably below about two thousand electron volts, and the relatively higher landing energy is preferably above about two thousand electron volts. Preferably, the lower similar layer is a gate insulation layer, the intervening dissimilar layer is a gate electrode layer, and the upper similar layer is a native oxide layer. In some embodiments, the lower similar layer and the upper similar layer are both electrically insulating layers and the intervening dissimilar layer is an electrically conductive layer. In other embodiments, the upper and lower similar layers each include a significant amount of oxygen and the intervening dissimilar layer does not include a significant amount of oxygen. The first and second readings are preferably made on characteristic X-rays that are emitted from the upper and lower similar layers when exposed to the first and second electron beams. Preferably, the first and second readings include at least one of thickness measurements and composition analysis.

According to another aspect of the invention there is described a system to measure a lower similar layer that is separated from an upper similar layer by an intervening dissimilar layer in an integrated circuit, the system. An electron beam generator directs a first electron beam having a first relatively lower landing energy at the integrated circuit, thereby producing first X-rays that are characteristic of the upper similar layer. The first relatively lower landing energy is sufficient to completely penetrate the upper similar layer and insufficient to completely penetrate the intervening dissimilar layer.

The electron beam generator also directs a second electron beam having a second relatively higher landing energy at the integrated circuit, thereby producing second X-rays that are characteristic of both the upper similar layer and the lower similar layer. The second relatively higher landing energy is sufficient to completely penetrate the upper similar layer, the intervening dissimilar layer, and the lower similar layer. A detector receives the first and second X-rays, and produces first and second signals that are representative of the first and second X-rays, respectively. A compensator subtracts the first signals that are characteristic of the upper similar layer from the second signals that are characteristic of both the upper similar layer and the lower similar layer, to produce readings that are characteristic of only the lower similar layer. In various embodiments, the first electron beam and the second electron beam are produced by two separate electron beam generators.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
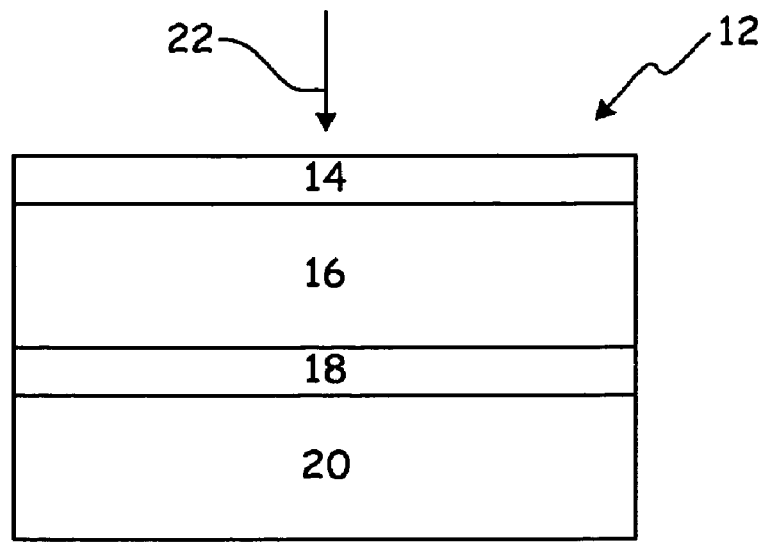
FIG. 1 is a cross sectional view of a substrate with two layers of similar composition separated by an intervening layer of dissimilar composition.

With reference now to FIG. 1, there is a cross sectional view of a substrate 10, depicting integrated circuit 12, having two layers 14 and 18 of similar composition that are separated by an intervening layer 16 of dissimilar composition. Additional underlying layers 20 may also be present as part of the overall piece, which is generally referred to herein as the substrate 10. As introduce above, it is desired to be able to take measurements, such as thickness measurements, on the underlying layer 18. However, at this step of the process, any such measurements of the underlying layer 18 tend to be confounded by emissions from the overlying similar layer 14.

Most preferably, both of the layers 14 and 18 have some property that distinguishes them from the intervening layer 16, and perhaps even the underlying layers 20, so that the only confounding influence on the desired readings is that between the layers 14 and 18.

As mentioned above, one such specific embodiment of the material stack depicted in FIG. 1 is that of a gate stack for an integrated circuit 12. In this specific embodiment, the underlying layers 20 represent a silicon or other semiconducting substrate, the layer 18 is a gate insulation layer, the layer 16 is a gate electrode layer, and the layer 14 is a native oxide layer. Although the present invention is applicable to other embodiments, the invention is described herein in specific reference to this particular embodiment.

The gate insulation layer 18 is preferably either a silicon oxide or a high k material as described above. The gate electrode layer 16 may be either a polysilicon layer or a metal containing layer. The native oxide layer 14 is an oxide of the material of the gate electrode layer 16, and tends to form immediately upon exposure of the gate electrode layer 16 to an oxygen bearing environment, such as air.

As mentioned above, it is desired to take a measurement of one or more properties of the gate insulation layer 18 at this point. However, because both the gate insulation layer 18 and the native oxide layer 14 tend to have similar properties, any such measurement of the gate insulation layer 18 tends to be confounded with a measurement of the native oxide layer 14.

One aspect of the present invention is preferably to take the measurements with a beam 22 with two distinct beam landing energies, or two beams with two landing energies, to distinguish the readings from the gate insulation layer 18 from the readings from the native oxide layer 14. The beam 22 is, in various embodiments, the same beam 22 that is operated at one energy first and then at another energy, or a single beam 22 that is quickly pulsed back and forth between two or more energies, or a single beam 22 that has different components that are multiplexed and operated at different energies. Each of these various and other contemplated beam 22 configurations are generally referred to as two separate beams 22 for convenience herein, even though it is appreciated that in some embodiments two separate beams 22 are not used. Alternately, a separate electron beam generator 25 can be used to produce a second beam 23 having a different landing energy than the first beam 22.

The native oxide layer 14 is preferably measured with a first beam 22 that has a relatively low landing energy, which landing energy is preferably sufficient to completely penetrate the native oxide layer 14, but which is insufficient to completely penetrate the gate electrode layer 16. The gate insulation layer 18 is preferably measured by a second beam 22 that has a relatively higher landing energy, which landing energy is preferably sufficient to completely penetrate the native oxide layer 14, the gate electrode layer 16, and the gate insulation layer 18.

The high and low landing energies referred to herein are generally dependant on the thickness and composition of the native oxide layer 14, gate electrode layer 16, and gate insulation layer 18. However, for current integrated circuit 12 designs, the low landing energy beam 22 preferably has a landing energy of less than about two thousand electron volts, and the high landing energy beam 22 preferably has a landing energy of more than about two thousand electron volts.

When the electron beams 22 impinge on the integrated circuit 12, they cause X-rays to be emitted from the material that is contacted by the electron beam 22. The X-rays have characteristics that are specific to the material within the layers 14, 16, and 18. By screening for the amount of X-rays emitted that have a specific characteristic, the composition and thickness of the layers 14, 16, and 18 can be determined. For example, if the native oxide layer 14 and the gate insulation layer 18 contain oxygen or nitrogen, and the intervening gate electrode layer 16, and perhaps additionally the underlying layers 20, do not, then looking for the amount of X-rays with characteristics of oxygen or nitrogen will tend to indicated the composition and thickness of the native oxide layer 14 and the gate insulation layer 18.

The readings from both the high energy and the low energy beams 22 are measured. The readings from the low energy beam 22 reports only the characteristics of the native oxide layer 14, because the low energy beam 22 does not penetrate down to the gate insulation layer 18. The readings from the high energy beam 22 reports the characteristics of both the native oxide layer 14 and the gate insulation layer 18, because it has sufficient energy to penetrate through both of those layers 14 and 18. The measurements from the low energy beam 22 are preferably subtracted from the measurement from the high energy beam 22, which tends to remove from the high energy beam 22 readings the influence from the native oxide layer 14. What is left of the high energy beam 22 readings is then attributable to the gate insulation layer 18.

Figure 2:
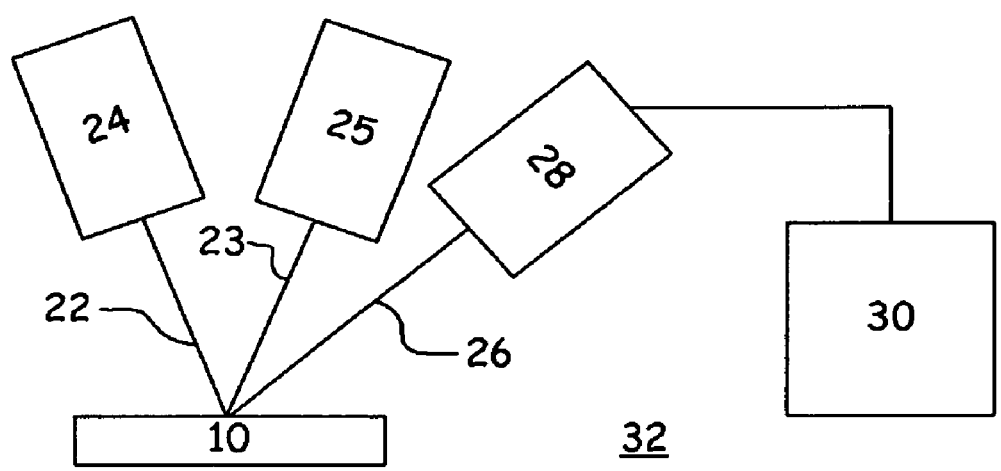
FIG. 2 is functional block diagram of a system for resolving confounded measurements taken on the substrate of FIG. 1, according to a preferred embodiment of the present invention.

A function block diagram of a system 32 according to a preferred embodiment of the present invention is depicted in FIG. 2. A beam generator 24 preferably generates the two beams 22 having high and low landing energies. The beams 22 impinge on the substrate 10, which produces characteristic X-rays 26, which are received by a detector 28. A compensator 30 quantifies the desired X-rays 26 as appropriate for the desired readings, and subtracts the low energy readings from the high energy readings to produce the desired readings on the lower film 18. Various embodiments of the present invention preferably use a highly controlled and spatially focused electron beam and X-ray directors, operated at two different landing energies.

The advantage of the methods according to the present invention is that the thickness of the gate insulation layer 18 can be measured more accurately and precisely using this two landing energy method than with prior art methods. Combining two landing energy measurements eliminates the uncertainty of the native oxide layer 14 thickness from the measurement.

The measurements for the high energy beam 22 and the low energy beam 22 are preferably taken on the same spot on the integrated circuit 12, although in some embodiments they could alternately be taken on different spots. The present invention enables the use of electron stimulated X-ray emission technology to measure oxide and high-k gate insulation layers 18 that are disposed under gate electrode layers 16. If there are more than two layers that have similar properties in the stack, then more than two different energies for the beam 22 can be used, where each energy penetrates to a different depth in the stack, and each successively higher landing energy penetrates through one successively deeper similar layer, so that the measurements from each successively deeper layer can be subtracted out, until only the measurements from a single layer, such as the deepest layer, remain.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of measuring a lower similar layer that is separated from an upper similar layer by an intervening dissimilar layer in an integrated circuit, the method comprising the steps of:

directing a first electron beam having a first relatively lower landing energy at the integrated circuit, the first relatively lower landing energy sufficient to completely penetrate the upper similar layer and insufficient to completely penetrate the intervening dissimilar layer, thereby producing first readings that are characteristic of the upper similar layer, directing a second electron beam having a second relatively higher landing energy at the integrated circuit, the second relatively higher landing energy sufficient to completely penetrate the upper similar layer, the intervening dissimilar layer, and the lower similar layer, thereby producing second readings that are characteristic of both the upper similar layer and the lower similar layer, and subtracting the first readings that are characteristic of the upper similar layer from the second readings that are characteristic of both the upper similar layer and the lower similar layer, to produce third readings that are characteristic of only the lower similar layer.

2. The method of claim 1, wherein the first electron beam and the second electron beam are produced at two different times by one electron beam generator.

3. The method of claim 1, wherein the first electron beam and the second electron beam are produced by pulsing one electron beam generator back and forth between the first relatively lower landing energy and the second relatively higher landing energy.

4. The method of claim 1, wherein the first electron beam and the second electron beam are produced by two separate electron beam generators.

5. The method of claim 1, wherein the first electron beam and the second electron beam are produced simultaneously by two separate electron beam generators.

6. The method of claim 1, wherein the relatively lower landing energy is below about two thousand electron volts.

7. The method of claim 1, wherein the relatively higher landing energy is above about two thousand electron volts.

8. The method of claim 1, wherein the lower similar layer is a gate insulation layer, the intervening dissimilar layer is a gate electrode layer, and the upper similar layer is a native oxide layer.

9. The method of claim 1, wherein the lower similar layer and the upper similar layer are both electrically insulating layers and the intervening dissimilar layer is an electrically conductive layer.

10. The method of claim 1, wherein upper and lower similar layers each include a significant amount of oxygen and the intervening dissimilar layer does not include a significant amount of oxygen.

11. The method of claim 1, wherein the first and second readings are made on characteristic X-rays that are emitted from the upper and lower similar layers when exposed to the first and second electron beams.

12. The method of claim 1, wherein the first and second readings include thickness measurement.

13. The method of claim 1, wherein the first and second readings include composition analysis.

14. A method of measuring a gate insulation layer that is separated from a native oxide layer by an intervening electrically conductive gate electrode layer in an integrated circuit, the method comprising the steps of:
   directing a first electron beam having a first relatively lower landing energy of less than about two thousand electron volts at the integrated circuit, the first relatively lower landing energy sufficient to completely penetrate the native oxide layer and insufficient to completely penetrate the intervening gate electrode layer, thereby producing first readings that are characteristic of the native oxide layer, wherein the first readings are made on characteristic X-rays that are emitted from the native oxide layer when exposed to the first electron beam,
   directing a second electron beam having a second relatively higher landing energy of more than about two thousand electron volts at the integrated circuit, the second relatively higher landing energy sufficient to completely penetrate the native oxide layer, the intervening gate electrode layer, and the gate insulation layer, thereby producing second readings that are characteristic of both the native oxide layer and the gate insulation layer, wherein the second readings are made on characteristic X-rays that are emitted from the native oxide layer and the gate insulation layer when exposed to the second electron beam, and
   subtracting the first readings that are characteristic of the native oxide layer from the second readings that are characteristic of both the native oxide layer and the gate insulation layer, to produce third readings that are characteristic of only the gate insulation layer.

15. The method of claim 14, wherein the first electron beam and the second electron beam are produced at two different times by one electron beam generator.

16. The method of claim 14, wherein the first electron beam and the second electron beam are produced by pulsing one electron beam generator back and forth between the first relatively lower landing energy and the second relatively higher landing energy.

17. The method of claim 14, wherein the first electron beam and the second electron beam are produced by two separate electron beam generators.

18. The method of claim 14, wherein the first electron beam and the second electron beam are produced simultaneously by two separate electron beam generators.

19. A system adapted to measure a lower similar layer that is separated from an upper similar layer by an intervening dissimilar layer in an integrated circuit, the system comprising:
   an electron beam generator adapted to direct a first electron beam having a first relatively lower landing energy at the integrated circuit, the first relatively lower landing energy sufficient to completely penetrate the upper similar layer and insufficient to completely penetrate the intervening dissimilar layer, thereby producing first X-rays that are characteristic of the upper similar layer,
   the electron beam generator further adapted to direct a second electron beam having a second relatively higher landing energy at the integrated circuit, the second relatively higher landing energy sufficient to completely penetrate the upper similar layer, the intervening dissimilar layer, and the lower similar layer, thereby producing second X-rays that are characteristic of both the upper similar layer and the lower similar layer,
   a detector adapted to receive the first and second X-rays and produce first and second signals that are representative of the first and second X-rays, respectively, and
   a compensator adapted to subtract the first signals that are characteristic of the upper similar layer from the second signals that are characteristic of both the upper similar layer and the lower similar layer, to produce readings that are characteristic of only the lower similar layer.

20. The system of claim 19, wherein the first electron beam and the second electron beam are produced by two separate electron beam generators.

* * * * *